United States Patent
Güttinger et al.

(10) Patent No.: US 6,342,077 B2
(45) Date of Patent: Jan. 29, 2002

(54) CEMENTABLE SHAFT PROSTHESIS

(75) Inventors: Werner Güttinger, Rudolfingen; Felix Mettler, Winterthur, both of (CH)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 09/797,519

(22) Filed: Feb. 28, 2001

(30) Foreign Application Priority Data

Mar. 1, 2000 (EP) .............................. 00810171

(51) Int. Cl.⁷ .................................................. A61F 2/36
(52) U.S. Cl. .................................. 623/23.25; 623/23.48
(58) Field of Search ........................... 623/23.25, 23.48, 623/23.19, 23.37, 23.46, 23.15; 606/95, 62

(56) References Cited

U.S. PATENT DOCUMENTS

| | | | |
|---|---|---|---|
| 5,074,879 A | * 12/1991 | Pappas et al. | 623/23.25 |
| 5,108,439 A | * 4/1992 | Morscher et al. | 623/23.48 |
| 5,458,651 A | * 10/1995 | Lawes | 623/23.25 |
| 6,241,772 B1 | * 6/2001 | Ling et al. | 623/23.15 |

* cited by examiner

Primary Examiner—Pedro Philogene
(74) Attorney, Agent, or Firm—Townsend and Townsend and Crew LLP

(57) ABSTRACT

The figures show a cementable shaft prosthesis (1) comprising a centering apparatus (2) of plastic which can be pushed on at its distal shaft end (3) and which forms a cavity (4) to the distal shaft end (3). Between the distal shaft end (3) and the centering apparatus (2) there exists a clamping connection which enables a deeper sinking in of the shaft end into the cavity in the distal direction. The clamping connection is achieved by a spigot (7) which is formed on at the centering apparatus (2) in the cavity (4) and which protrudes in into a conical bore (5) of the shaft end (3) in the proximal direction.

10 Claims, 3 Drawing Sheets

CEMENTABLE SHAFT PROSTHESIS

BACKGROUND OF THE INVENTION

The invention relates to a cementable shaft prosthesis comprising a centering apparatus of plastic which can be pushed on at its distal shaft end and which forms a cavity to the distal shaft end, with a conical clamping connection existing between distal shaft end and the centering apparatus which permits a deeper sinking in of the distal shaft end into the cavity in the distal direction.

A centering apparatus for the distal end of a cementable prosthesis shaft which can be pushed onto the distal end and forms a cavity for the distal end in order that the distal end can sink in deeper into the cavity to avoid fissures in the hardened cement is shown in patent application GB-A-2 104 391. Plastics such as polyethylene are used as the material for the centering apparatus.

This proposed embodiment has the disadvantage that the distal end, which is formed conically, must be machined to within very narrow tolerances in its outer contour in order to ensure a clamping in the axial direction and a subsequent slipping when the axial force increases. This kind of clamping at the same time causes such a strong sealing action that a ventilation bore at the lowest point of the cavity is proposed. A further disadvantage consists in that thick shaft ends, which would be desirable for obtaining a uniformly thin cement jacket in the marrow chamber cavity, have large surface portions with a relatively large half cone angle of the surface to the shaft axis in the distal region. If a clamping with guide surfaces which lie closely in contact is provided in this region, large axial forces and ring stresses arise at a cement pouch which surrounds the shaft and the centering apparatus after the hardening of the bone cement due to the relatively large half cone angle in the event that the shaft sinks in further into the cavity.

SUMMARY OF THE INVENTION

The object of the invention is to improve the prosthesis and the centering apparatus in this regard. This is achieved in accordance with the independent claim 1 in that the distal shaft end has a conical bore in the proximal direction in which a spigot which is formed on at the centering apparatus in the cavity forms the clamping connection.

The invention has the advantage that the outer contour of the distal prosthesis end has no guiding function any longer and that the cavity of the centering apparatus can be held without cement through a weak line contact between its proximal circumferential edge and the surface of the shaft. A further advantage consists in the reliability of the clamping and positioning of the centering apparatus on the spigot, since the cone angle can be chosen freely and since a conical bore can be economically produced in the distal shaft end to within narrow tolerances.

Advantageous further developments of the invention result from the subordinate claims 2 to 10.

In the manufacture of the centering apparatus in an injection molding tool particularly narrow pairing tolerances result in the clamping region between the spigot and the conical bore, since the geometry of the spigot is likewise produced as a bore due to the shape inversion in the injection mold. The manufacture and the monitoring of the tolerances are thus simpler at both parts, shaft end and centering apparatus.

The half cone angle of the conical bore can be chosen between 0.5° and 2.5° depending on the material of the shaft and the centering apparatus and in accordance with the geometry of the spigot. In the case of a metallic shaft and a centering apparatus of plastic, for example of PMMA (polymethyl methyl acrylate), the half cone angle can lie between 1.2° and 1.6°.

If the spigot has two stages with different diameters and the graduation in relation to the axial distance is chosen such that it coincides with the half cone angle of the conical bore, then two axially spaced guiding and clamping zones arise during the pushing on of the centering apparatus which oppose a resistance force F in the axial direction corresponding to the friction and to the half cone angle between the conical bore and the spigot which increases overproportionally with increasing dipping in of the shaft tip. A dipping in is practically possible only because the stages of the spigot deform radially inwardly. If the spacing of the stages is chosen such that at first only one stage is contiguous at the conical bore and if this stage can be more easily deformed radially, because for example it is formed of only a few ribs, then at first only a slight axial resistance force arises in the pushing on of the centering apparatus, which only increases much more strongly when the second stage is also radially inwardly deformed during the further dipping in of the distal shaft tip. This means that during the pushing on the centering apparatus holds itself on the shaft tip and develops a noticeable resistance when the centering apparatus has reached a predetermined position aligned with its spigot. The prosthesis shaft can then be introduced with the centering apparatus into a marrow chamber of a tubular bone which is filled with bone cement and is guided at its distal end by at least three fins of the centering apparatus.

The desired position of the centering apparatus is signalled in an even more marked way during the pushing on if the conical bore has a run-in cone with a somewhat larger half cone angle and the second stage is contiguous at this steeper cone and must first be radially deformed at this steeper cone for the further penetration into the conical bore. The cavity in the centering apparatus and the axial resistance force are dimensioned such that the distal shaft end can later dip in into the centering apparatus by several millimeters after the pushing on and cementing in without the jacket of the centering apparatus, which is enclosed by the bone cement, experiencing impermissible forces in the axial direction.

In a femur shaft prosthesis it is advantageous due to the medially lying femur head when in the introduction of the shaft in the marrow chamber cavity the centering apparatus supports the shaft towards the lateral by a fin. For this reason it is furthermore advantageous when a rotational securing which is independent of the dipping in depth and which permits a pushing on of the centering apparatus only when a fin is oriented laterally is provided between the shaft tip and the centering apparatus in the cavity. When the prefabricated centering apparatus itself consists of PMMA, a homogeneous cement pouch with the bone cement results after the cementing in of the prosthesis which permits a later sinking in of the shaft, without impermissible stresses arising in the cement pouch in the region of the distal shaft tip.

BRIEF DESCRIPTION OF THE DRAWINGS

In the following the invention will be described with reference to exemplary embodiments. Shown are.

DESCRIPTION OF THE PREFERRED EMBODIMENTS

Figure 1:
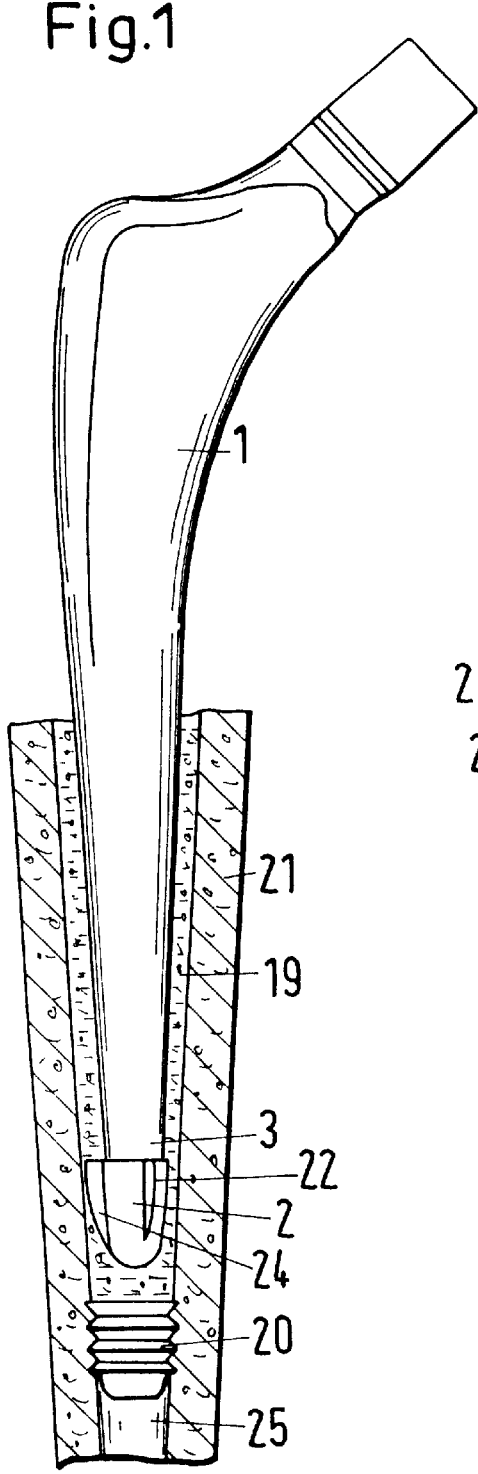
FIG. 1 schematically, a view of a femur shaft prosthesis with a centering apparatus.

The figures show a cementable shaft prosthesis 1 comprising a centering apparatus 2 of plastic which can be pushed on at its distal shaft end 3 and which forms a cavity 4 to the distal shaft end 3. Between the distal shaft end 3 and the centering apparatus 2 there exists a clamping connection which enables a deeper sinking in of the shaft end into the cavity in the distal direction. The clamping connection is achieved by a spigot 7 which is formed on at the centering apparatus 2 in the cavity 4 and which protrudes in into a conical bore 5 of the shaft end 3 in the proximal direction.

In the figures identical reference symbols are used for identical function features.

In FIG. 1 a femur shaft prosthesis 1 is provided at its distal shaft end 3 with a centering apparatus 2 which can be pushed on. The femur bone 21 is provided in its marrow chamber cavity 25 with a marrow chamber blocking 20 which seals against bone cement 19 which is filled in in liquid form. The prosthesis 1 and the centering apparatus are lowered together into the liquid bone cement 19 until a predetermined penetration depth has been reached. During the lowering the distal shaft end 3 is centered within the marrow chamber cavity 25 by fins 22, 24. In this, one fin 24 is oriented towards the lateral.

Figure 2:
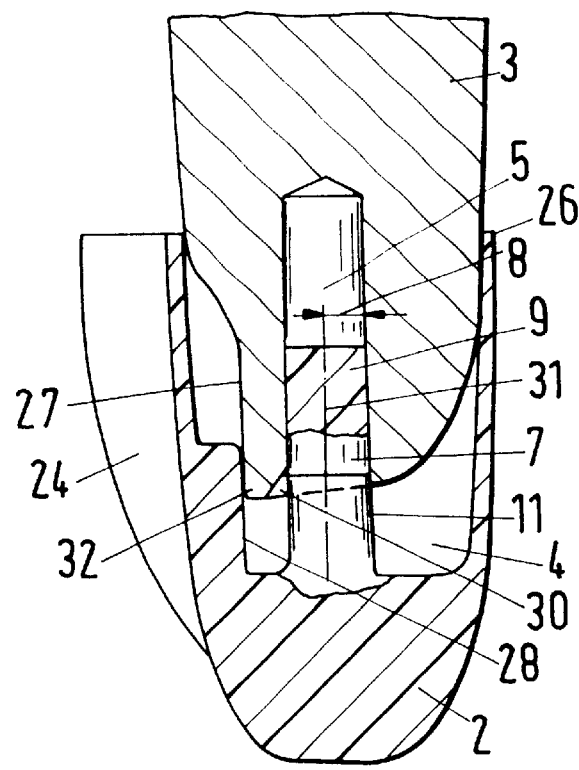
FIG. 2 schematically an enlarged section of the shaft end of FIG. 1 with the centering apparatus.
Figure 3:
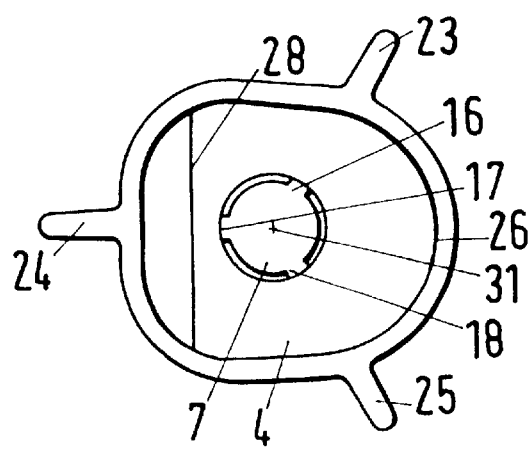
FIG. 3 schematically a plan view of the centering apparatus of FIG. 2.

The centering apparatus 2 in FIGS. 2 and 3 has with its upper edge 26 only a weak line contact with the shaft end 3 in order to prevent an intrusion of liquid bone cement. The actual fixing takes place through a spigot 7 which is formed on in a cavity 4 at the centering apparatus 2 and which is clamped in a conical bore 5 which is provided in the proximal direction at the shaft end 3. For a metal shaft for example a conical bore 5 with a half cone angle 8 of 1.43° is provided. The spigot has a first stage with attached ribs 16, 17, 18 which are limited in the unstressed state to a diameter 10 which lies somewhat below the diameter 12 of a following second stage 11. The position of the spigot 7 in FIG. 2 corresponds to a desired pushing on position, in which the ribs 16, 17, 18 are already radially inwardly deformed to such an extent that a desired clamping force against drawing out is achieved. At the same time the second stage 11 is centered with its slightly larger diameter in a run-in cone 30 of the conical bore 5 and forms an additional and easily noticeable resistance against the further penetration of the spigot 7. Only at a substantially greater axial force of the shaft end 3 is the second stage 11 also radially inwardly deformed and the shaft end 3 can dip in deeper into the cavity 4 of the centering apparatus 2 against a predetermined resistance force. The cavity 4 and the conical bore 5 are dimensioned such that the shaft can dip in by a further several millimeters into the centering apparatus 2 against a higher resistance after the pushing on of the centering apparatus 2. This "jump" in the resistance has the advantage that the centering apparatus 2 is not pushed further onto the shaft during the guiding and lowering of the prosthesis shaft 1 in the liquid bone cement 19. In order to be able to place the centering apparatus on only when a fin 24 is oriented laterally, a recessed surface 27 which ends in a nose 32 is provided parallel to the shaft axis 31 at the shaft end 3. For this the centering apparatus has a suitable guiding surface 28 in the cavity 4 which prevents rotation.

Figure 4:
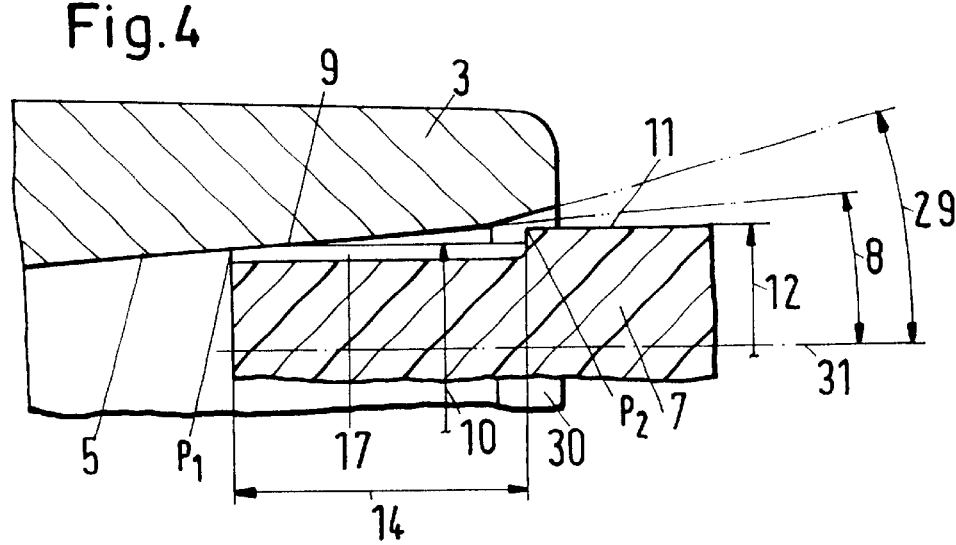
FIG. 4 schematically, greatly enlarged and exaggerated in the angles, a section of a spigot at the beginning of the lying in contact in a conical bore.
Figure 5:
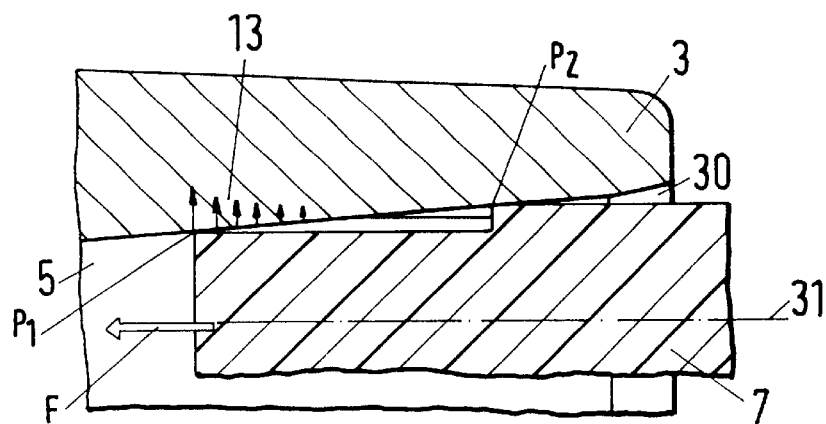
FIG. 5 schematically, the arrangement of FIG. 4 at the beginning of the lying in contact of a second stage in the conical bore.
Figure 6:
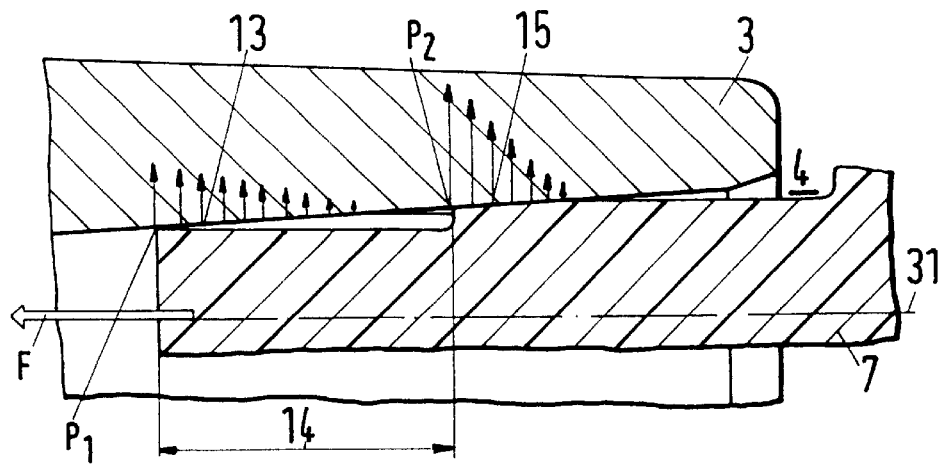
FIG. 6 schematically, the arrangement of FIG. 5 on further introduction of the spigot.

An arrangement is shown in FIGS. 4, 5, 6 in which the run-in cone 30 does not contribute with its half cone angle 29 to the increase in the resistance force F in the axial direction. During the pushing on of the spigot 7, the first stage 9 with a point P1 at diameter 10 of the rib 17 first makes contact with the conical bore 5, whereas the axial distance 14 for a point P2 with diameter 12 of the second stage 11 is dimensioned such that the point $P_2$ does not yet make contact with the conical bore 5. During the continuation of the pushing on movement the ribs 17 are radially inwardly deformed at point $P_1$ and there arises a clamping and guiding zone 13 (FIG. 5) with a weakly increasing clamping force. Only when the second stage 11, which opposes a substantially greater resistance, is contiguous at the conical bore is a desired position for the pushing on achieved. The resistance force in the axial direction is so great that the shaft 1 and the centering apparatus are not pushed further together by the centering apparatus during the lowering of the shaft and its guide. In FIG. 6 the shaft 3 has moved in against a greater resistance force F into the cavity 4, with the resistance force F being dimensioned such that no impermissible tension stresses in the axial direction are produced by the centering apparatus 2 at the cement pouch 19 which surrounds it.

Figure 7:
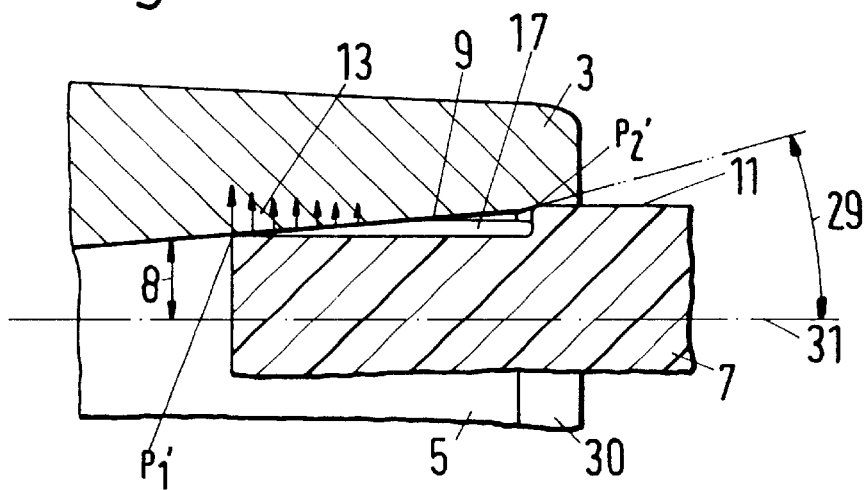
FIG. 7 schematically, a further arrangement as in FIG. 2 in which the second stage first lies in contact at a run-in cone.

In FIG. 7, analogously to FIG. 5, the state at the end of the pushing on of the centering apparatus is shown. The spigot 7 has already been deformed at its first stage 9 at points $P_1'$ and forms clamping and guiding zones 13, whereas points $P_2'$ of the second stage 11 lie in contact at the run-in cone 30 with half cone angle 29. In the short steeper cone section, which must be passed through by the point $P_2'$ until it lies in contact on the conical bore 5 with half cone angle 8, a jump 33 in the resistance force F takes place. A reliable axial positioning in the pushing on of the centering apparatus also lies in this region.

Figure 8:
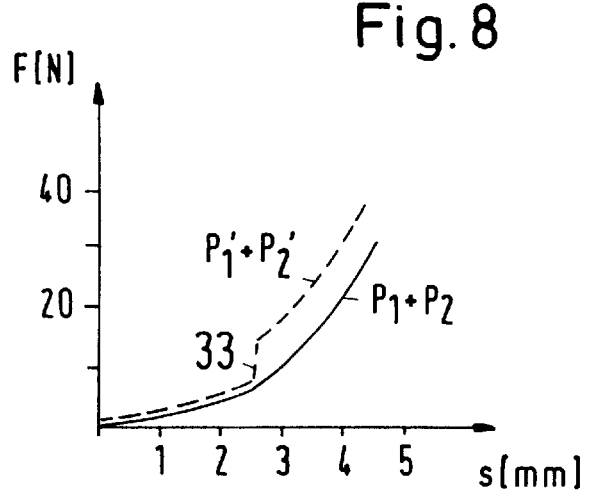
FIG. 8 schematically, a graph of the resistance force in the axial direction during the pressing in of a spigot.

FIG. 8 shows a graph in which the resistance force F is plotted against a distance S in the axial direction. For an arrangement in accordance with FIG. 5 a steeper rise of the resistance force F takes place with the additional engagement of point $P_2$. For an arrangement in accordance with FIG. 7, which corresponds to a characteristic curve in broken lines, a jump 33 in the force rise at first takes place with the additional engagement of a point $P_2'$, and is followed by a steeper rise.

Figure 9:
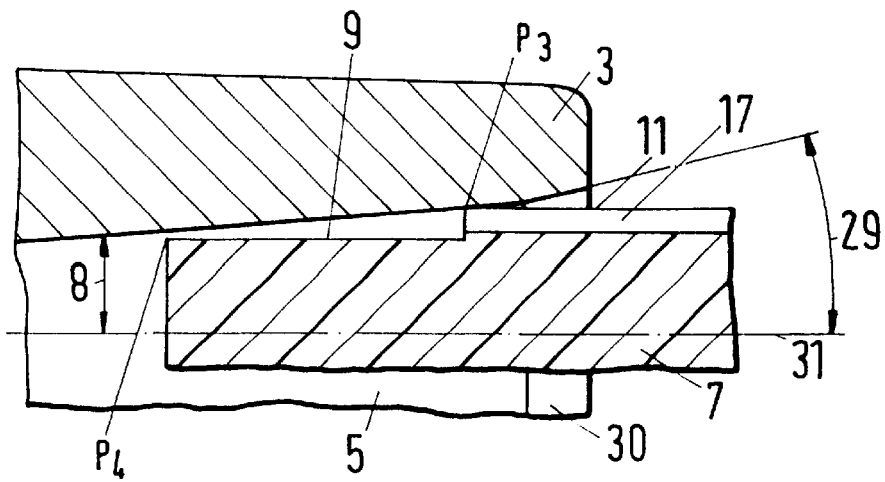
FIG. 9 schematically, an arrangement analogous to FIG. 5 in which the second stage lies as the first of the two in contact in the conical bore with a point $P_3$.

FIG. 9 shows a further arrangement in which at first the second stage 11, which is provided with ribs 17, comes with a point $P_3$ into engagement with the conical bore 5, whereas the first stage with a point $P_4$ still has a clearance to the conical bore 5. During the continuation of the placing on, in this case the rib 17 is first inwardly deformed in order to clamp the spigot 7. Only when the point $P_4$ lies in contact at the conical bore 5 is a bend with steeper rise of the resistance force F produced in a continuation of the movement. Quite generally the magnitude of the axial resistance force can be defined by the shaping or, respectively, through the contour, the diameters 10, 12 and the axial spacing 14 of the two stages 9, 11, which determine their yielding in the radial direction, and through the size of the half cone angle 8.

What is claimed is:

1. Cementable shaft prosthesis comprising a centering apparatus (2) of plastic which can be pushed on at its distal shaft end (3) and which forms a cavity (4) to the distal shaft end (3), with a conical clamping connection (6) existing between distal shaft end (3) and the centering apparatus (2) which permits a deeper sinking in of the distal shaft end (3) into the cavity (4) in the distal direction, characterized in that the distal shaft end (3) has a conical bore (5) in the proximal direction in which a spigot (7) which is formed on at the centering apparatus (2) in the cavity (4) forms the clamping connection (6).

2. Shaft prosthesis comprising a centering apparatus in accordance with claim 1, characterized in that the centering apparatus (2) is manufactured as an injection molded part using an injection molding tool.

3. Shaft prosthesis comprising a centering apparatus in accordance with claim 1, characterized in that the conical bore (5) has a half cone angle (8) between 0.5° and 2.5°.

4. Shaft prosthesis comprising a centering apparatus in accordance with claim 3, characterized in that the conical bore (5) has a half cone angle (8) between 1.2° and 1.6°.

5. Shaft prosthesis comprising a centering apparatus in accordance with claim 1, characterized in that the spigot (7) has a first stage (9) at which a second stage (11) with a greater diameter (12) adjoins in order to produce two clamping and guiding zones (13, 15) with an axial spacing (14) at the spigot (7).

6. Shaft prosthesis comprising a centering apparatus in accordance with claim 5, characterized in that the first stage (9) is formed of a plurality of projecting ribs (16, 17, 18) which oppose a lower resistance to their radial deformation than the second stage (11).

7. Shaft prosthesis comprising a centering apparatus in accordance with claims 1, characterized in that the possible sinking in depth of the shaft (3) amounts to more than 1 mm after the pushing on and clamping of the centering apparatus (2).

8. Shaft prosthesis comprising a centering apparatus in accordance with claims 1, characterized in that the centering apparatus has at least three centering fins (22, 23, 24) in order to make the shaft (3) alignable during the insertion into a marrow chamber cavity (25) to the walls of the latter.

9. Shaft prosthesis comprising a centering apparatus in accordance with claim 8 for a femur shaft, characterized in that one fin (24) can be oriented towards the lateral in that a form fitted rotational securing (27, 28) is additionally in engagement between the shaft end (3) and the centering apparatus (2) within the cavity (4).

10. Shaft prosthesis comprising a centering apparatus in accordance with claim 1, characterized in that the centering apparatus consists of PMMA.

* * * * *